United States Patent [19]

Fichera

[11] 4,276,890
[45] Jul. 7, 1981

[54] TOBACCO SMOKING INHIBITOR

[76] Inventor: Anthony T. Fichera, 319 Palos Verdes Blvd., #310, Redondo Beach, Calif. 90277

[21] Appl. No.: 82,987

[22] Filed: Oct. 9, 1979

Related U.S. Application Data

[63] Continuation-in-part of Ser. No. 29,107, Apr. 11, 1979, abandoned.

[51] Int. Cl.$^3$ .............................................. A61K 9/68
[52] U.S. Cl. ................................. 131/270; 424/48; 426/3; 426/660
[58] Field of Search ........................ 426/3–6, 426/536, 548, 660; 424/48; 131/2

[56] References Cited

U.S. PATENT DOCUMENTS

| | | | |
|---|---|---|---|
| 3,156,569 | 11/1964 | Griffin et al. | 426/536 |
| 3,293,045 | 12/1966 | Griffin | 424/230 |
| 3,296,079 | 1/1967 | Griffin | 424/49 |
| 3,338,718 | 8/1967 | Olson | 426/536 |
| 3,376,317 | 4/1968 | Stephens et al. | 426/536 |
| 3,409,441 | 11/1968 | Bouchard et al. | 426/548 |
| 3,446,629 | 5/1969 | Stephens et al. | 426/536 |
| 3,903,900 | 9/1975 | Wolt et al. | 131/17 R |

FOREIGN PATENT DOCUMENTS

| | | | |
|---|---|---|---|
| 840306 | 1/1976 | Belgium. | |
| 1963736 | 6/1971 | Fed. Rep. of Germany | 426/548 |
| 2613500 | 10/1976 | Fed. Rep. of Germany. | |
| 50/25018 | 5/1966 | Japan | 426/548 |
| 46/6829 | 8/1967 | Japan | 426/548 |
| 1364103 | 8/1974 | United Kingdom. | |
| 1540648 | 2/1979 | United Kingdom. | |

OTHER PUBLICATIONS

Fernaroli's Handbook of Flavor Ingredients, 2nd Ed. (1971), CRC Press, Cleveland, Ohio, p. 179 Ethyl Maltol (up to 50 ppm), pp. 327 Maltol (up to 90 ppm).
C. A. 76 #70329q (1972) 78, #70236r (1973) 79 #76032p (1973) 81, #62300d (1974) 82, #14177t (1975) 82, #15330z (1975).
C. A. 83 #190530q (1975) 86, #21718f (1977) 86, #145665f, #145679 (1977) 87, #4312x, #4313y (1977) 88, #168595p (1978).
Larson, P. S., Silvette, H., Tobacco, Experimental & Clinical Studies Supplement 2, Williams & Wilkins Co. Balt. Md 1971:246–248, 543–545 p. 543, esp. Gould (1953), noted that medicated lozenge curbed smoking, Benzocaine Flavored with Saccharin, Licorice, Ginger, Anise, Wintergreen, Peppermint, Coriander & Cloves (No Citation Given).
Opdyke, D. L. J. Food Cosmet. Toxicol. 13, Suppl. 805–806 (1975), Ethyl Maltol, Suppl. 841 (1975), Maltol.

*Primary Examiner*—Shep K. Rose

[57] ABSTRACT

A method of inhibiting or destroying the desire to smoke tobacco products which comprises administering for an extended period of time a gamma pyrone selected from the class of maltol and ethyl maltol and in a quantity initially of not less than about 500 milligrams per day. By incorporating a maltol in relatively large amounts in gum, candy, or other physiologically acceptable media, the desired amount of maltol can be taken by reasonable daily consumption of such media. Releasing the maltol in the mouth at least 10 minutes for about 12 to 15 times per day is important. A lozenge or troche that lasts over 10 minutes in the mouth and releases ethyl maltol at a rate of excess of about 0.2 mg./min. is preferred. When this is done the pyrone should be administered at more than about 75 mg./day.

10 Claims, 1 Drawing Figure

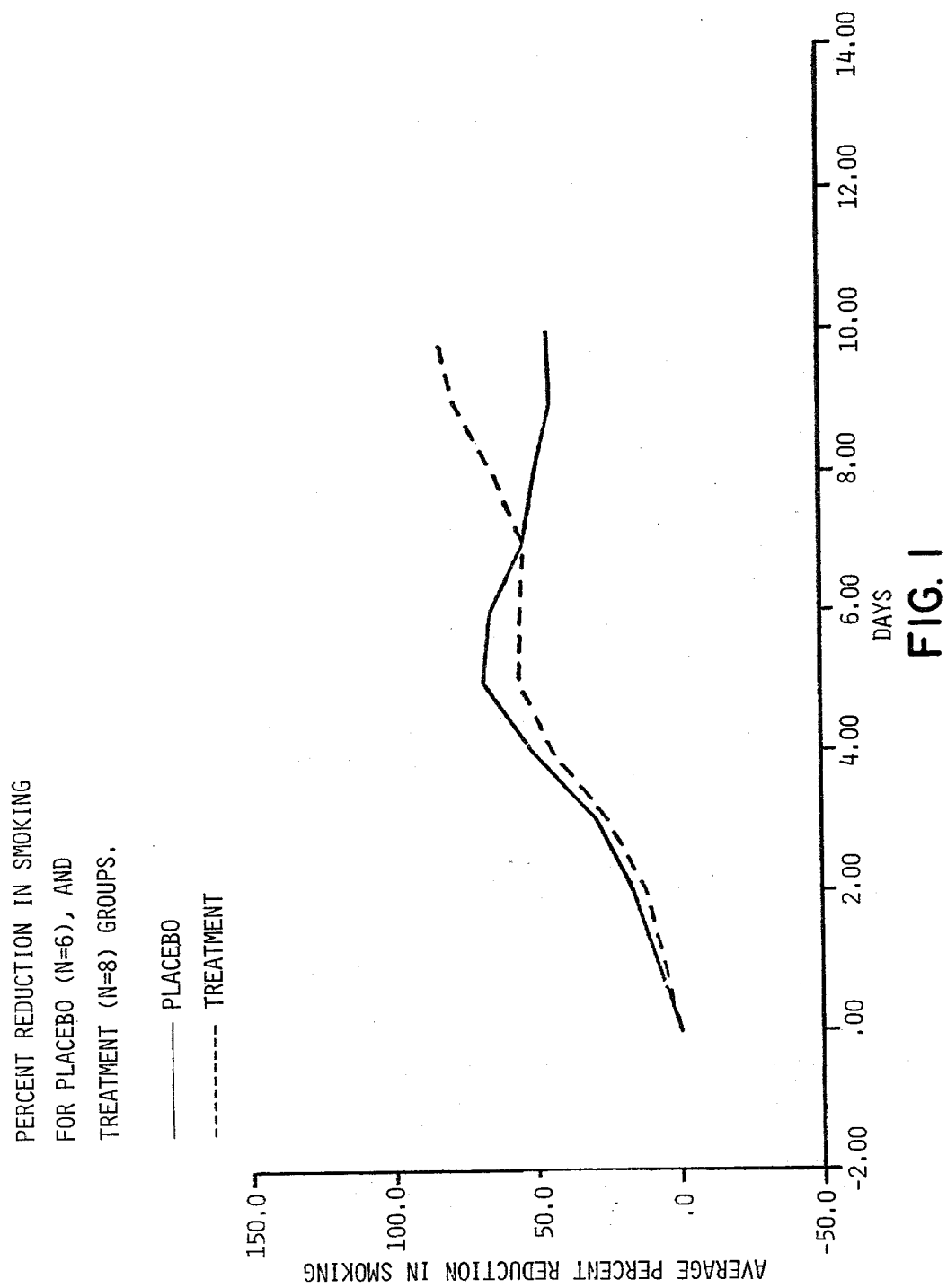

TOBACCO SMOKING INHIBITOR

This application is a continuation-in-part of Ser. No. 29,107 filed Apr. 11, 1979, now abandoned.

BACKGROUND AND PRIOR ART

Cigarette smoking has been recognized as a major public health problem for more than ten years. Despite a high degree of public awareness of this fact, the proportion of smokers has decreased but slightly in the past ten to fifteen years. A 1975 survey sponsored by the United States Department of Health, Education and Welfare reported that 39.3% of adult males and 28.9% of adult females in this country were current smokers, averaging 23 cigarettes a day and 19 cigarettes a day, respectively. (*Adult Use of Tobacco*—1975, United States Public Health Service, 1976.) The extraordinary persistence of the smoking habit is further highlighted by the high degree of awareness among smokers of the health hazard. Two-thirds of the smokers surveyed were concerned about possible effects of cigarette smoking on their own health.

Despite the high level of awareness of health hazard, the smoking habit remains extraordinarily persistent and difficult to break. The above cited survey reported that 61% of current smokers had made at least one serious attempt to quit smoking. A full 90% of current smokers had either tried to quit smoking or would probably do so if there were an easy way to stop.

The smoking habit is perceived as being difficult to break. Recidivism is high. Yet, it is clear that there is both a need and a demand of long standing for a convenient and relatively easy method for aiding smokers in reducing or eliminating cigarette consumption.

The smoking habit is maintained and reinforced by a combination of social, psychological and physiological responses whose nature and relative importance and interactions remain poorly understood. The rate of consumption among smokers commonly fluctuates in response to worry, stress and anxiety. In addition, physiological adaptations to the pharmacological actions of nicotine cause sensations of discomfort and/or unease when the smoker attempts to quite smoking. Although the dynamics of the interaction of the pharmacological, physiological and psychological factors contributing to the smoking habit are as yet poorly understood, it is well known that the habit is difficult to break. Prior art methods for stopping or reducing smoking include the exercise of will power, various psychological conditioning techniques, and the administration of various substances designed to counteract or substitute the supposed habituating effects of nicotine.

A comprehensive survey of prior art methods for reducing smoking behavior is Larson, P.S. and Silvette, H., *Tobacco Experimental and Clinical Studies, Supplement* 2, The Williams and Wilkins Company, Baltimore, 1971. The exercise of will power, or simply quitting smoking without the use of any aids, substitutes or other devices, remains at least as successful as any other method. A related method is that of tapering off, involving a gradual reduction in number of cigarettes smoked over a period of time. The method is less reliable because much smoking behavior is unconscious and success requires very close monitoring of the actual number of cigarettes smoked. Various commercial devices, such as filters of graded capacity, have been marketed as aids to the tapering off method.

A variety of techniques have been advanced involving some sort of aversion conditioning. One approach is to provide the smoker with a substance which creates a bad taste in the mouth or interacts with the cigarette smoke to produce unpleasant sensations in the mouth. For example, mouth washes and lozenges containing silver nitrate, silver acetate and/or copper sulfate have long been recommended, either alone or in combination with psychoactive drugs or psychotherapy. Similarly, vegetable bitters such as tulip poplar bark, quassia and ginseng root have been stated to render the tobacco taste unpleasant. The effectiveness of such methods is considered to be questionable. A major disadvantage of such self-administered aversion treatments is the east of discontinuing the course of treatment. Some success has been achieved in an in-patent setting with other forms of aversion therapy, such as psychotherapy coupled with administration of electric shocks. However, these methods are expensive, as well as time consuming, and if the patient reacquires the habit, he or she will be less likely to submit to the therapy a second time.

Other forms of treatment are based upon the supposed habituating effects of nicotine. One approach in the prior art has been to disassociate the mechanical and sensory aspects of the smoking habit from the pharmocological effects of nicotine by providing for the administration of a maintenance dose of nicotine while removing or discontinuing the use of cigarettes. A chewing gum containing nicotine has been developed and tested with apparent success (Brantmark, B., et al, Psychoparmacologia Berl.) 31, 191 (1973); (Ferno, O., et al., Psychopharmacologia, Berl.) 31, 201 (1973). A difficulty with the method is that a physiological dependence upon nicotine remains and until such dependence is overcome, the opportunity to resume smoking at the original pretreatment dose level is very high. In addition, the method fails to solve the long term health problems presented by nicotine administration.

A substantial amount of research and commercial activity has been associated with the use of lobeline. The pharmocological action of lobeline is described as a weak nicotine-like action, but devoid of the pleasurable sensations of nicotine and apparently discontinuable without a withdrawal syndrome. Therefore, the use of lobeline for tobacco dishabituation is based upon a plausible substitution hypothesis. In addition, lobeline has an extremely bitter taste and when administered in combination with nicotine produces highly disagreeable symptoms. Consequently, there is an element of aversion conditioning in lobeline therapy systems. Lobeline may be administered by intramuscular or subcutaneous injection, or perorally, in tablets, chewing gums, lozenges and the like. However, when studied in controlled double blind tests against placebo, lobeline has been found to be ineffective, i.e., no more effective than placebos (Merry, J. and Preston, G., *The Practitioner* (May, 1963), pp. 629–631).

The results with lobeline point up two procedural difficulties in experimental design of any test of a method or product for reducing smoking behavior. First, there is in all studies a large placebo effect for any agent which is administered. The dynamics of this placebo effect are not known. However, the placebo effect alone may result in a decrease of as much as 50% in the amount and frequency of cigarettes smoked. Second, the psychological state of patients who enter treatment or experimental studies of an anti-smoking treatment must be taken into account. For example, a smoker who expresses a desire to quit but says he cannot do so on his own, may, in fact, be subconsciously committed to continued smoking, or may be satisfied with a reduction of 50%. Consequently, the circumstances under which test subjects are chosen must be considered with care.

The compounds 3-hydroxy-2-methyl-4-pyrone (maltol) and 3-hydroxy-2-ethyl-4-pyrone (ethyl maltol) are known for enhancing certain food flavors when present in optimally small amounts. U.S. Pat. No. 3,156,569 discloses the use of maltol as a flavor enhancer in combination with glutamate salts. U.S. Pat. No. 3,271,167 discloses artificial beef flavored gravy and broth compositions comprising alpha ketoglutarate, inosinate, glutamate and maltol. U.S. Pat. No. 3,293,045 discloses the use of maltol to enhance flavorings imparted by methyl salicylate, anethole and cinnamaldehyde. U.S. Pat. No. 3,296,079 discloses the use of maltol to mask the aftertaste of artificial sweeteners. Up to 400 parts per million of maltol in the final sweetened product may be used, but in larger amounts, maltol contributes a flavor note of its own. Optimally, lower concentrations of maltol are recommended. The maximum amount may be employed if bitter ingredients, for example stannous fluoride, are to be masked by the sweetening agent. U.S. Pat. No. 3,338,718 discloses that the addition of maltol in animal feeds up to 200 grams per ton to feed improves the rate of weight gain. U.S. Pat. No. 3,376,317 and 3,446,629 disclose that ethyl maltol is about six times as effective a flavor enhancer as maltol itself. Ethyl maltol is useful as a flavor enhancer in the range from one to 100 parts per million of the final food product. At higher concentrations, the food product begins to have an aroma contributed by the ethyl maltol itself. Ethyl maltol is disclosed to have an inherent flavor, not otherwise described, except that in sweet foods it creates a velvet mouth sensation.

Maltol has been identified by Saguma, H., et al., *Agric. Biol. Chem.* 42, 359 (1978) as a component of the mixture resulting from cellulose pyrolysis. The compound was said to be responsible for a pleasant caramel or burnt sugar-like aroma. Shigematsu, H., *Agric. Biol. Chem.* 35, 1751 (1971) and Shumacher, J. N., et al., *J. Agric. Food Chem.* 1977, 310, identified maltol in the water-soluble portion of cigarette smoke.

Maltol and ethyl maltol have been employed as additives for tobacco products and tobacco substitutes. U.S. Pat. No. 3,903,900, Wolt, et al., discloses the addition of up to 600 parts per million of maltol in a composition designed to enhance the flavor and aroma of tobacco. British Pat. No. 1,364,103 discloses an artificial smoking composition designed to replace tobacco. Such compositions may contain maltol or ethyl maltol up to 1.5% by weight, as a flavor and aroma imparting constituent.

Relative to the present invention, the concentrations of maltol or ethyl maltol in the ingested product are quite low; on the order of 1–400 ppm. An apparent exception is found in Belgian Pat. No. 840,306 by Grieske et al. Maltol was disclosed as a chelating agent useful for removing stains from teeth when applied topically to the teeth in a dentifrice, mouthwash or chewing gum at a concentration of up to 5% (50,000 ppm) for a maximum of one minute. Twice daily application was disclosed. Used as disclosed, such prior art compositions provide a maximum of 150 mg maltol per application assuming a 3 g stick of gum containing 5% maltol. Such use does not provide a minimally effective dose of maltol to be effective in the present invention, as described in detail infra. In fact, the topical application and short duration in the mouth indicate that substantially less than the calculated maximum dose of maltol would be ingested.

The value of maltol and ethyl maltol as food additives is greatly enhanced by their low toxicity. Maltol is included on the Flavor and Extracts Manufacturer's Association list of compounds generally recognized as safe for food additive purposes. Both compounds have been judged to be safe for an average daily intake of 1 mg per kg and 2 mg per kg for maltol and ethyl maltol, respectively. See Opdyke, D. L. J., *Food Cosmet. Toxicol,* 1975, 13, Suppl. 805 and 841. Consumption of as much as 1.5 grams per day of maltol appears to be completely harmless. Pharmacological studies have not been extensive. Both maltol and ethyl maltol are rapidly absorbed after oral administration and rapidly excreted, primarily as glucuronide and ethereal sulfate conjugates. In mice, maltol, 75 mg/kg, decreased spontaneous motor activity by approximately 50%. Ethyl maltol was also inhibitory, but somewhat less potent. Both compounds inhibited convulsions produced by pentylenetetrazole or strychnine while potentiating hexobarbital-induced sleeping time. See Aoyagi, N., *Chem. Pharm, Bull.* 221008 (1974). The dosage used in these experiments were 300 to 500 mg per kg, extremely high in view of the acute $LD_{50}$'s of 820 and 910 mg per kg. for maltol and ethyl maltol respectively in mice. Oxygen intake by rat brain cortex slices in vitro was not affected by 1 maltol or ethyl maltol. These observations make it clear that maltol and ethyl maltol have pharmacological activity, although the nature of this activity is not clearly delineated at present.

SUMMARY OF THE INVENTION

The present invention relates to the discovery that the administration of maltol or ethyl maltol at appropriate dosage levels and rates, significantly reduces the tobacco consumption of habitual smokers. In a preferred embodiment, finely divided ethyl maltol is distributed in a chewing gum base, which when chewed by the subject, results in a gradual release of ethyl maltol into the oral cavity. When administered in appropriate amounts over a period of several days, there results a gradual decrease in the number of cigarettes smoked and the length of time they are smoked. The reduction appears to be spontaneous and does not appear to be accompanied by the typical symptoms of nicotine withdrawal. Reductions in the frequency and quantity of smoking have been observed in test subjects who were unaware that their smoking behavior was monitored. Objectively, test subjects treated according to the dosage regimen to be described appear to be spontaneously reducing their consumption of cigarettes gradually over a period of several days beginning about the second or third day of treatment, without complaining about aversive reactions, or unpleasant side ffects. Subjectively, test subjects experience a reduced desired to smoke, tend to neglect the opportunities to light up a cigarette and tend to leave cigarettes unsmoked in the ashtray after a few puffs. The effect is sufficiently subtle that a smoker is sometimes unaware that his tobacco consumption rate was decreased until such point as the lowered consumption rate becomes obvious. For smokers sincerely desiring to reduce or eliminate their smoking, the effect of the treatment is most gratifying. However, for smokers who are not psychologically committed to giving up smoking, the effects may be alarming. It is of course, possible to override the effects of the treatment by conscious effort to smoke at the pre-treatment rate. While doing so does not result in serious discomfort, the smoker does not experience sufficient satisfaction from smoking at the pre-treatment rate to do so without considerable conscious effort.

The actual dosage to be employed may be adjusted by the individual, since effective dose varies according to body weight and to individual responsiveness. A typical daily dose effective for a 70 kg adult male would be 1,000 mg, of ethyl maltol per day. Maltol is $\frac{1}{4}$ to 1/6 as effective as ethyl maltol and dosage must be adjusted accordingly. The foregoing dose amounts to 14.28 mg ethyl maltol per kg body weight per day. Ethyl maltol appears to be effective when administered systemically. Since ethyl maltol is rapidly metabolized and excreted, the most effective dosage strategy is one which maintains a continuous dose above the threshold level of effectiveness. Preferably, maltol or ethyl maltol is released slowly in the oral cavity via a sustained release vehicle such as a chewing gum. A typical daily dose should be spread over the waking hours, for example, in about seven to eight increments. Over a course of ten days of such treatment, there is observed a gradual reduction in tobacco consumption, measured by number of cigarettes smoked and proportion of length smoked, to about 50% over the first four to six days. Placebo studies give a similar result; followed however, by a gradual increase over the ensuing days. By contrast, after seven to ten days of treatment according to the present invention, tobacco consumption is further reduced, in most instances to 100%. Reduction to 75% or greater is commonly observed. When rapid reductions of greater than 50% are observed, physiological responses to nicotine withdrawal occur, suggesting that long term effectiveness of the treatment would be enhanced by a gradual tapering off mediated by a downward adjustment of the ethyl maltol dosage.

DETAILED DESCRIPTION OF THE INVENTION

Maltol and ethyl maltol share in common the gamma pyrone ring structure. Gamma pyrones having flavor enhancing and pharmacologic properties essentially similar to maltol and ethyl maltol are contemplated as within the scope of the invention. Ethyl maltol is the more effective of the commercially available gamma pyrone tested to date, being four to six times more effective, on a weight basis, than maltol.

Smoking behavior is complex and includes cigarette, pipe and cigar smoking. Both from the standpoint of habituation and of health hazard, cigarette smoking is considered to be the most serious. It is contemplated that the treatment method described herein will be effective to inhibit all forms of smoking behavior and combinations thereof, involving the consumption of tobacco. For convenience, the ensuing discussion focuses on cigarette smoking, as exemplary of smoking behavior in general. Tobacco consumption is a function the number of cigarettes smoked and the proportion of each cigarette smoked. Reduction of consumption is measured by comparison with a smoker's pretreatment consumption rate. All data used herein are expressed as percent reduction, i.e., the differential between pretreatment and current smoking consumption rate divided by the pretreatment rate, times 100. All rates are calculated to take into account both the number of cigarettes smoked and the proportion of each smoked.

The gamma pyrones are effective in inhibiting tobacco consumption when administered perorally. Since maltol and ethyl maltol are rapidly metabolized and excreted, the preferred mode of administration is one which spreads the daily dose over the waking hours, by administration of a series of incremental doses during the day. It has been found that administration is considerably more effective if the gamma pyrone is retained in the mouth for a period of time during administration of such an incremental dose. The advantages of retention in the mouth are observed when the incremental dose is released therein over a period of at least ten minutes and preferably 20-30 minutes. The preferred method of such administration is a slowly dissolving lozenge, troche, or chewing gum, in which the gamma pyrone is dispersed. Incomplete data suggest the possibility that systemic oral administration is effective. If so, other forms of systemic administration such as subcutaneous injection could be employed, especially when combined in a sustained release formulation.

The effective dosage varies with individual responsiveness to the treatment. Higher doses are used in the initial stages of treatment than in the later stages. Initially, dosage of ethyl maltol in the range of 500 mg to 1500 mg may be employed, with 800 mg to 1200 mg preferred. Individual responsiveness to gamma pyrones varies widely, with women and younger people tending to be more responsive and thus requiring lower daily doses.

The daily dose, to be optimally effective, must be divided into a series of incremental doses, preferably about 7-8 per day. In the preferred embodiment, each incremental dose is administered from a time release vehicle such as a slowly dissolving troche or chewing gum. Chewing gum has been found to be a most effective vehicle. It has the advantage or permitting the user to adjust his dose rate by chewing a desired length of gum stick for the appropriate time interval, at least 10 minutes and preferably 20 to 30 minutes. For example, gum containing 156 mg ethyl maltol per stick could be used to administer 7 to 8 incremental doses. The rate of ethyl maltol released by a lozenge, trouche or chewing gum, should be in the range of 2 to 16 mg/min, preferably 4 to 8 mg/min. It is noteworthy that 156 mg of gamma pyrone in a 1.75 g stick of gum is a concentration of about 90,000 parts per million, which is several orders of magnitude greater than amounts disclosed for any flavoring or flavor enhancement purpose.

The number of incremental doses should be calculated to provide a minimum of 20 to 70 mg of ethyl maltol per dose, depending upon the individual factors described supra. The minimum effective dose of maltol is 4 to 6 times greater. For ethyl maltol, to provide a minimum dose in a 3 g stick of gum would require as little as 0.66% ethyl maltol. The maximum quantity would be about 300 mg in a 1 g stick, roughtly 30%. The preferred range of ethyl maltol concentrations in a chewing gum is between 5% and 15%. The best mode presently contemplated for a chewing gum composition contains 156 mg ethyl maltol per 1.75 g stick (8.9%).

Duration of treatment may be as little as ten days, preferably 20 to 30 days. As might be expected with a complex behavior such as smoking, where psychological and social factors play a major role in addition to individual variations in nicotine susceptibility and responsiveness to gamma pyrone, the rate of smoking reduction during treatment is highly variable. Typically, a gradual reduction to about 50% to the pretreatment rate is observed over the first four to six days. Frequently, little or no reduction is observed for the first two days, although occasionally a dramatic reduction is observed almost immediately. In the ensuing seven to ten days, further reductions, typically 70 to 100%, are observed. Reduction below the 50% level in the first 3-5 days is sometimes accompanied by the physiological (but not psychological) symptoms of nicotine withdrawl, such as vertigo, alimentary distress, diuresis, scotoma and disorientation. Such symptoms have never been observed in non-smoking control subjects using the same gamma pyrone dosages. To minimize the effects of nicotine withdrawal, it is preferred to lower the gamma pyrone dosage once the smoking level has decreased to 50%, in order to accomplish the subsequent reduction at a somewhat lower rate. The entire course of treatment is therefore extended somewhat, preferably to about 20 to 30 days total. The lack of physiological nicotine withdrawal symptoms during the first 50% of smoking reduction is consistent with the observations of others that reductions of up to 50% are achievable by placebo administration without appreciable side effects (Merry, J. and Preston, G., supra; Sutherland, A., et al., *J. Consulting Clin. Psych.* (August 1975) pp. 443-447). It appears that habitual smokers normally consume sufficient tobacco to maintain a daily dose about twice that needed to prevent withdrawal symptoms. Therefore, only reductions greater than 50% can be regarded as clinically significant.

The objective findings are straightforward. In the majority of cases, there is a gradual reduction in smoking, both in number of cigarettes lit and amount of each smoked, the percent reduction eventually increasing to substantially more than 50%. A rate of reduction varies considerably from one individual to the next and is dose related. A remarkable feature is that the smoking reduction occurs whether or not the subject is aware of the purpose for which the gamma pyrone is administered. In initial experiments, subjects were simply asked to self-administer the desired dosage and to report all of their observations. Some subjects remained unaware of their reduced smoking for one to two days, until the phenomenon was inescapable, as for example, when the same pack of cigarettes was being used two days in a row.

The subjective effects of the gamma pyrone treatment are the most interesting and informative. Most remarkably, the reduction in cigarette consumption is accompanied by none of the common effects of quitting smoking, such as anxiety, nervousness or restlessness. If anything, subjects appear after reductions greater than 70% to have a reduced level of anxiety and often experience an increased sense of purpose and self worth. These subjective responses are observed even in the phase of treatment where minor physiological nicotine withdrawal symptoms can be observed. The gamma pyrone treatment appears to disassociate the physiological from the psychological affects of nicotine habituation, and to somehow remove the latter.

The principal side effects of the treatment are those to be expected when a large concentration of a potent flavor enhancer is present in the mouth over a period of several days. The taste of a gamma pyrone such as ethyl maltol is difficult to described, in fact, varying considerably depending upon what other flavors are in the mouth or have previously been in the mouth. Similarly, the tastes of other substances are affected, depending on how recently the gamma pyrone has been administered. Certain substances and flavor combinations produce unpleasant and bitter sensations in the presence of the large quantities of gamma pyrone used in the treatment method. For this reason, a chewing gum or troche formulation must be free of trace amounts of bitter agents such as amino acids and tannins, and highly aromatic flavorings such as cinnamon or wintergreen. When properly formulated, without added flavorings except for optional mild fruit flavorants such as apple, the gamma pyrone chewing gum or troche will have a pleasant flavor. Initially, some subjects experience a sharp taste and salivation will be stimulated. The taste of tobacco products, as with other substances, depends upon the length of time since the last dose of gamma pyrone was administered. Some subjects, after chewing a stick of ethyl maltol gum, find the initial taste of a cigarette to be pleasurable. At most other times, the cigarette flavor may be disagreeable.

Perhaps the most profound effect experienced by subjects under treatment is a pronounced, generalized enhancement of the taste and olfactory sensorium. All flavors and odors appear intensified. Subjects become aware of and sensitive to off odors and flavors in food and drink. Foodstuffs containing such off flavor elements tend to be avoided. Subjects display a decided preference for the better grades of coffee, tea and alcoholic beverages. Bitter tastes, as in beer, are poorly tolerated. One subject, an avid beer drinker, discontinued the treatment program because it interfered with a customary after hours beer.

The foregoing effects are experienced by smoking and non-smoking subjects alike. When when treatment is discontinued, the flavor enhancement affects disappear. Physiological effects attributable to gamma pyrone administration have not been observed.

EXAMPLE 1

The formulation of a slowly dissolving troche is described herein. Alternative formulations known in the art can be readily devised to accomplish the following goals: the troche should be slowly soluble in the mouth, preferably lasting about 15 minutes, retaining its physical integrity during that period; the flavor should be mild, preferably a fruit flavor; and the troche should be only slightly sweetened, if at all.

The troche was composed primarily (greater than 90% by weight) of a high molecular weight polysaccharide, a non-hygroscopic hydrolyzed cereal solid having a dextrose equivalent of less than 15, such as "Mor-Rex", code 1918, Trademark CPC International, Inc., Englewood Cliffs, New Jersey. Dissolution time was controlled by incorporating up to 1% of a hydrophobic starch such as modified waxy maize starch (Dry-Flo, National Starch Company). Waxy maize starches are also known as amioca starch and are composed almost entirely of highly branched amylopectin. The effect, on dissolution time, of small amounts of waxy maize starch in a 1.2 gram troche is given by the following table;

| Percent by Weight Waxy Maize Starch | Oral Dissolution Time (minutes) |
|---|---|
| 0 | 6 |
| ½ | 8 |
| ¾ | 10 |
| 1 | 15 |

Addition of greater than 1% waxy maize starch made the composition unduly rubbery and difficult to manipulate.

The troches were made essentially by conventional candy making techniques. The polysaccharide and starch were first dry blended to substantial uniformity. About 3-4% by weight of water was added to the dry powder to form a thick paste. This paste was then heated to produce a uniform viscous melt. Maltol or ethyl maltol were added to this melt as saturated solutions in boiling water. The water solubility of the gamma pyrones is somewhat limited. For example, one gram of ethyl maltol requires 6 ml of water at 100° C. to dissolve completely. Since the water content of the mixture must be kept low, the amount of ethyl maltol which can be incorporated is about 3-4%, and preferably about 1% by weight of the troche. Since ethyl maltol is volatile, especially at elevated temperatures, it is essential to minimize the length of time the mass is held at the elevated temperature once the gamma pyrone is added. Alternatively, the entire process can be carried out in a suitable pressure apparatus. Alternatively, ethyl maltol and other gamma pyrones may be added in alcoholic solution wherein they are somewhat more soluble, permitting higher final concentrations of gamma pyrone in the finished product.

Flavoring materials may be added if desired. Small amounts of mild fruit flavors are preferred, spicy flavors are to be avoided.

After mixing to evenly distribute the components, the molten candy mass was then handled in substantially the same manner as a taffy, in that it was pulled to a uniform smooth microstructure and optimum water content. The taffy may be rolled or extruded into ropes or strips and re-gelled at about 160° F., cut to the desired weight troches and regranulated before wrapping to protect against moisture loss. Conventional equipment for handling, casting or stamping troches of desired size and shape may be used.

The resulting troche was a hard, tough article primarily composed of polysaccharide and containing 1-5% by weight of ethyl maltol depending upon the formulation as described. Individual troches were of sufficient size to provide an adequate incremental dose of ethyl maltol when retained in the mouth and allowed to dissolve gradually over the approximately 15 minute lifetime of the troche.

EXAMPLE 2

The formation of a chewing gum for administering a gamma pyrone according to the invention is next described. Crystaline ethyl maltol was ground and sieved to 300 mesh. The ground particles acquired a static charge, tending to float upwards. In practice, it was possible to sieve the particles upwards, collecting only those which passed through the 300 mesh screen.

The ground particles were mixed at 45° C. with a plastic chewing gum base, until evenly distributed throughout the mass. The chewing gum base was selected to be free of amino acids, tannins and other flavoring elements capable of combining with gamma pyrone to yield bitter off flavors. The rate of release of gamma pyrone into the oral cavity is a function of the rate of solution of the gamma pyrone as the gum is chewed. The rate of solution is controlled by the size of the gamma pyrone particles dispersed in the gum. Optimally, for ethyl maltol, particles in the size range from 300 to 400 mesh when dispersed in such a matrix, are dissolved in the mouth in about 30 minutes. The gamma pyrone must be dispersed throughout the gum in particulate form to provide the desired sustained release effect, particles smaller than 300-400 mesh dissolved more slowly, so that the incremental dose was delivered more slowly. Larger particles dissolved more rapidly than desired so that the dose was delivered in an undesirably short time. Larger particles also tended to recrystallize into yet larger aggregates during storage.

A refined, bland chewing gum base, obtained from Adams Sour Apple gum, (Warner-Lambert, Inc., Morris Plains, N.J.) was heated to 45° C. in a 100 gram batch. Ethyl maltol, 300 to 400 mesh, 6.66 grams, was added to the chewing gum base with thorough mixing to provide an even distribution of particles throughout the mass. The mass was then rolled into individual 3 gram sticks and allowed to cool. Alternatively, the mass was rolled as a single thin rectangular slab, allowed to cool, then cut into 3 gram sticks. The individual sticks were then wrapped with plastic or treated paper to prevent storage loss of ethyl maltol due to sublimation at room temperature. Each 3 gram stick contains 200 mg of ethyl maltol.

The ethyl maltol dose was administered simply by chewing an appropriate amount of the gum for at least 10 and preferably 15 minutes. For many subjects, an adequate dose was administered by chewing a half a stick of gum at one time. The flavor was described as pleasant and occasionally as sharp, depending on the antecedent flavors in the subject's mouth.

EXAMPLE 3

Single Dose Response

The effect of a single dose of ethyl maltol in the range from 100 mg to 1,200 mg was tested on thirty volunteer subjects who were smokers. As a control, an additional ten smokers were given an inert placebo, a similar candy or gum laced with ascorbic acid and citric acid to impart a medicinal flavor. Subjects treated with a single dose of placebo showed no effect on their smoking habit. Subjects receiving greater than 300 milligrams of ethyl maltol experienced an immediate overt negative reaction to cigarettes. The threshold of effectiveness varied with the individual's age, sex, weight, smoking history, and habits. The threshold dose also varied with the mode of administration, being somewhat lower if delivered in a chewing gum over a ten to fifteen minute period rather than ingested in tablet form. However, as a general rule, a single dose of less than 300 mg. produced no definitive effect. By contrast, for substantially all individuals, a definitive result of reduced desire to smoke cigarettes was noted when the dosage was greater than 500 mg. A definite result was a substantially reduced level of smoking, lasting anywhere from a few hours to two days. For some subjects, physiological symptoms of nicotine withdrawal were noted. Increased effectiveness was observed with increasing dose up to about 1,200 mg but at doses greater than 1,200 mg no addition advantage was noted. These studies established the existence of a critical threshold dose level below which the effectiveness of ethyl maltol as a tobacco smoking inhibitor was not observed. In subsequent tests where the gamma pyrone was administered in a dose series extending over several days, daily doses of less than about 300 mg per day were similarly ineffective.

EXAMPLE 4

Extensive tests were made of individual smokers of varied age, smoking history, and sex in a course of treatment extending over several days. All smokers tested in this experiment were initially naive as to the purpose of the test or the expected effect. The subjects volunteered for the tests after being told that the material is safe according to FDA food additive standards and that they were to report all observed effects. So far as can be ascertained none of the subjects deduced the true purpose of the test until the effects were made obvious by substantial involuntary reduction in their smoking activities. Subjects were interviewed before the dosage course to insure that they were in general good health. Interviews were also conducted during and after the dosage course, at least every third day to ascertain what physiological or psychological effects were experienced. No side effects were noted during or after the treatment cycle.

As a control, five non-smoker volunteers were tested according to the same regimen, receiving varying quantities of ethyl maltol in excess of 500 mg. per day for periods of several days. Observations and interviews showed no psychological or physiological effects.

Several individuals from the original test series volunteered for additional testing. In all such instances, a treatment free period of three weeks to three months was interposed between tests.

Results of the tests are shown in Table 1. Subjects are identified by number. The original, naive tests are identified by the letter "a" following the subjects' number. Subsequent test series are identified sequentially by "b" and "c", where appropriate.

All subjects except nos. 10 and 11 received ethyl maltol in a chewing gum with instructions to chew for at least 10 minutes, and preferably 15 minutes. Subjects 10 and 11 received ethyl maltol in tablet form, rather than by sustained release in the mouth. The results suggest that systemic administration of the gamma pyrone was partially effective. However, the experiments did not rule out the possibility that the results were due to retention of a portion of the dose in the mouth, as by chewing or sucking the tablets.

TABLE 1

| 1 Subject No. | 2 Age | 3 Sex | 4 Smoking History (years) | 5 Dosage unit/day | 6 Est. Dosage Ingested per day (mg.) | 7 Dose Course (days) | 8 Cigarette Consumption per day at start | 9 Cigarette Consumption per day at end | 10 Percentage Reduction | 11 Change in Smoking Pattern per cig. |
|---|---|---|---|---|---|---|---|---|---|---|
| 1a | 50 | M | 35 | 4 sticks | 800 | 16 | 50 | 15 | 70% | Reduced to light-up |
| 2a | 54 | M | 40 | 4½ Stks | 900 | 12 | 50 | 0 | 100% | — |
| 2b | 54 | M | 40 | 4 sticks | 800 | 20 | 35 | 10-15 | 70-80% | Approx. ½ |
| 2c | 54 | M | 40 | 3½ Stks | 700 | 30 | 35 | 5 | 90% | Approx. ½ |
| 3a | 58 | M | 40 | 7½ Stks | 1500 | 25 | 70 | 0 | 100% | — |
| 3b | 58 | M | 40 | 3½ Stks | 700 | 8 | 50 | 15-20 | 60-70% | Varied |
| 4a | 45 | M | 30 | 6 sticks | 1200 | 8 | 40 | 0 | 100% | — |
| 4b | 45 | M | 30 | 5 sticks | 1000 | 4 | 30 | 5 or less | 80%+ | Less than ½ |
| 5a | 40 | M | 25 | 3½ Stks | 700 | 14 | 50 | 7-10 | 90%+ | Less than ¾ |
| 6a | 23 | FM | 6 | 3 sticks | 600 | 1 | 20 | Reduced to ½ pack for following 2 wks. | | |
| 7a | 39 | FM | 13 | 5 sticks | 1000 | 7 | 30 | 7-10 | 65-70% | Less than ½ |
| 7b | 39 | FM | 13 | 4 sticks | 800 | 20 | 17-20 | 7-10 | 41-68% | Less than ½ |
| 7c | 39 | FM | 13 | 3½ Stks | 700 | 40 | 15 | 7-8 | 41-53% | Reduced to 2-3 puffs |
| 8a | 28 | FM | 9 | 4 sticks | 800 | 1 | 20 | 5 | 75% | Less than ½ |
| 8b | 28 | FM | 9 | 3 sticks | 600 | 1 | 20 | 7 | 40-50% | Less than ½ |
| 9a | 40 | FM | 25 | 4 sticks | 800 | 5 | 50 | 10-12 | 75-80% | Less than ¾ |
| 10a | 36 | M | 19 | 6 tablets | 1200 | 10 | 40 | 10-12 | 70-75% | Reduced to 3-4 puffs |
| 11a | 32 | M | 14 | 5 tablets | 1000 | 15 | 30 | 17-18 | 40-43% | Less than ¾ |
| 12a | 43 | M | 20 | 5 sticks | 1000 | 8 | 30 | 3-4 | 87-90% | Reduced to 3-4 puffs |
| 13a | 44 | M | Non Habit Smoker | 5 sticks | 1000 | 2 | Non-habit Smoker | Not able to finish cigarette during dose course | | |

EXAMPLE 5

Daily Rates of Smoking Reduction

Subjects who participated had prior knowledge of the purported effect of the treatment. They were asked to test a new dosage form and told that a "cure" was not necessarily to be expected in this test. The dosage was 1,000 mg/day of ethyl maltol divided over eight pieces of slowly dissolving lozenges, made essentially as described supra. Subjects administered their own dosage without supervision. The tests were designed and supervised by the inventor but carried out by intermediaries, in order to maximize the opportunity for objective evaluation of symptoms, and to minimize any possibility of investigative bias influencing the results. (True double blind tests are impossible because the gamma pyrone flavor is distinctive and virtually impossible to mask). Subjects were all in generally good health, and were selected to represent a variety of ages, occupational stresses, and personal life styles.

The results of the tests are shown in Table II. Levels of tobacco consumption were calculated taking into account the number of cigarettes smoked and the proportions smoked. They are expressed as percent reduction from the pretest smoking level.

TABLE II

| | | Chart records reduction in smoking level (%). | | | | | | | | | |
|---|---|---|---|---|---|---|---|---|---|---|---|
| | | Day No.: | | | | | | | | | |
| Subject | Sex | 1 | 2 | 3 | 4 | 5 | 6 | 7 | 8 | 9 | 10 |
| 1. | M | — | 5 | 10 | 40 | 30 | 60 | 50 | 70 | 80 | 85 |
| 2. | M | — | 15 | 20 | 50 | 80 | 95 | 40 | 55 | 70 | 90 |
| 3. | M | — | 5 | 5 | 10 | 10 | 20 | 20 | 40 | 70 | 85 |

TABLE II-continued

| | | Chart records reduction in smoking level (%). | | | | | | | | | |
|---|---|---|---|---|---|---|---|---|---|---|---|
| | | Day No.: | | | | | | | | | |
| Subject | Sex | 1 | 2 | 3 | 4 | 5 | 6 | 7 | 8 | 9 | 10 | |
| 4. | M | — | 10 | 40 | 65 | 85 | 95 | 90 | 75 | 80 | 90 | |
| 5. | M | — | 5 | 10 | 5 | 10 | 15 | 20 | 15 | 20 | 30 | (heavy alcohol consumption). |
| 6. | F | 10 | 30 | 60 | 75 | 60 | 50 | 65 | 70 | 65 | 70 | |
| 7. | F | — | 10 | 30 | 70 | 90 | 70 | 85 | 90 | 95 | 90 | |
| 8. | F | — | 5 | 15 | 30 | 50 | 25 | 30 | 55 | 90 | 80 | |
| 9. | F | — | 10 | 15 | 10 | 35 | 20 | 45 | 50 | 65 | 70 | |
| 10. | F | — | 20 | 45 | 70 | 95 | | Discontinued | | | | ("beer tasted funny"). |

Numbers in blocks represent percentage reduction in smoking, taking into account lengths of cigarettes smoked.

EXAMPLE 6

Placebo Experiments

During the same time period that the studies in Example Five were conducted, two groups of smokers were administered a placebo dosage comprising the same basic candy lozenge, but lacking any gamma pyrone and containing ascorbic and citric acids to impart a sharp, medicinal flavor.

Placebo Group 1 was composed of volunteers recruited from a coffee break group, who were given essentially the same information as the active test group of Example Five. The test was administered by an intermediary individual who was not aware that the dose was a placebo. The results are shown in Table III.

TABLE III

PLACEBO GROUP 1

| | | Day No.: | | | | | | | | |
|---|---|---|---|---|---|---|---|---|---|---|
| Subject | Sex | 1 | 2 | 3 | 4 | 6 | | 7 | 8 | 9 | 10 |
| 1. | M | — | 0 | 0 | 0 | 0 | | | Discontinued | | |
| 2. | M | — | 5 | 10 | 10 | 20 | 40 | | Discontinued | | |
| 3. | F | — | 0 | 0 | 0 | 0 | | | Discontinued | | |
| 4. | F | — | 5 | 5 | 15 | 45 | 40 | 45 | 45 | 40 | 30 |
| 5. | F | — | 15 | 35 | 55 | 65 | 70 | 60 | 55 | 55 | 55 |

Numbers in blocks represent percentage reduction in smoking, taking into account lengths of cigarettes smoked.

Placebo Group Two was composed of students of a college professor who had himself participated in earlier tests of efficiency (Subject No. 2 of Example Three), and who administered the tests on Group Two without knowledge that a placebo dose was used. The volunteer test subjects of Group Two were given essentially the same pre-test information as Group One and the active test group of Example Five, although it is possible that the professor's enthusiasm for the treatment could have influenced the results, shown in Table IV.

TABLE IV

PLACEBO GROUP 2

| | | Day No.: | | | | | | | | |
|---|---|---|---|---|---|---|---|---|---|---|
| Subject | Sex | 1 | 2 | 3 | 4 | 5 | 6 | 7 | 8 | 9 | 10 |
| 1. | M | — | 15 | 20 | 60 | 95 | 90 | 60 | 60 | 45 | 45 |
| 2. | M | — | 25 | 60 | 85 | 90 | 100 | 60 | 50 | 40 | 40 |
| 3. | M | — | 20 | 30 | 55 | 65 | 60 | 55 | 40 | 50 | 55 |
| 4. | F | — | 10 | 10 | 5 | — | 5 | 10 | — | 5 | 0 |
| 5. | F | — | 15 | 20 | 35 | 45 | 30 | 40 | 45 | 30 | 40 |

Numbers in blocks represent percentage reduction in smoking, taking into account lengths of cigarettes smoked.

It was concluded that tests of a smoking inhibitor treatment are subject to a substantial placebo effect. The magnitude of the effect is clearly variable with individuals and with test design. The placebo effect is large and may account for up to 50% reduction in smoking level.

Comparison of the data of Example Five and the placebo groups supports the conclusion that the gamma pyrone treatment result in substantially decreased smoking levels over the placebo effect, in a ten day course of treatment. This conclusion is further substantiated by analysis of variance. For such analysis, individual tests that were either incomplete or which presented unusual circumstances were discarded. Results from placebo groups one and two were pooled. The average percent reduction in smoking is plotted in FIG. 1, for the treatment and the placebo groups. Analysis of variance for days seven through ten, where the treatment in placebo groups began to diverge, indicated that the treatment group was indeed significantly different from the placebo group.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of inhibiting tobacco smoking of smokers without physiological symptoms of nicotine withdrawal comprising smoking while awake during the waking hours of the day and administering to such a smoker 500 mg to 1500 mg total daily dose of ethyl maltol or maltol as a gamma pyrone divided into several incremental doses during the waking hours of the day, each incremental dose being retained in the smoker's mouth and released therein over a period of at least 10 minutes, for at least about 5 to 10 days, for a total of about 20 to 30 days or at least until there results either of a gradual decrease in the number of cigarettes smoked and the length of time they are smoked or until such point as the lowered tobacco consumption rate becomes obvious.

2. The method of claim 1 wherein the daily dose is divided into seven to eight incremental doses.

3. The method of claim 1 wherein the incremental dose is released over a period of 20 to 30 minutes.

4. The method of claim 1 wherein the gamma pyrone is ethyl maltol.

5. The method of claim 4 wherein the daily dose of ethyl maltol is 800 mgs to 1200 mgs per day.

6. The method of claim 1 wherein the gamma pyrone dose is contained in a composition comprising a physiologically acceptable inert carrier capable of providing sustained release of the gamma pyrone in the smoker's mouth over a time period of at least 10 minutes, in unit dosage form containing from 20 mg to 300 mg gamma pyrone per unit dose.

7. The method of claim 6 wherein the carrier comprises about 90 parts by weight of high molecular weight polysaccharide having a dextrose equivalent of less than 15 and 1 part by weight waxy maize starch together with sufficient water to dissolve the gamma pyrone, blended to uniform composition and formed into troches weighing 3 g to 5 g each.

8. The method of claim 6 wherein the sustained release carrier comprises a chewing gum base and the gamma pyrone is ethyl maltol in particulate form, the particle size being 300 to 400 mesh, blended to uniform composition and divided into stick weighing 2 to 4 gms each.

9. The method of claim 8 wherein the total daily dose is divided into 7 to 8 incremental doses.

10. The method of claim 9 wherein each chewing gum stick weighs 1.75 grams and contains 156 mg. of ethyl maltol, and each stick constitutes one incremental dose, and is chewed over a period of 20 to 30 minutes.

* * * * *